United States Patent [19]
Baude
[11] 3,932,448
[45] Jan. 13, 1976

[54] 2-(ALKOXYCARBONYLAMINO)-1-BENZIMIDAZOLECARBOXYLIC ACID ESTERS WITH HYDROXYALIPHATIC ACIDS AND DERIVATIVES THEREOF

[75] Inventor: Frederic J. Baude, Wilmington, Del.

[73] Assignee: E. I. Du Pont de Nemours & Company, Wilmington, Del.

[22] Filed: July 19, 1973

[21] Appl. No.: 380,601

Related U.S. Application Data

[63] Continuation-in-part of Ser. No. 116,247, Feb. 17, 1971, abandoned, which is a continuation-in-part of Ser. No. 776,273, Nov. 15, 1968, abandoned.

[52] U.S. Cl. .............................. 260/309.2; 424/273
[51] Int. Cl.² .............................. C07D 235/32
[58] Field of Search .............................. 260/309.2

[56] References Cited
UNITED STATES PATENTS
3,673,210 6/1972 Daum et al. .............................. 260/309.2

*Primary Examiner*—Natalie Trousof

[57] ABSTRACT

Substituted 2-alkoxycarbonylamino-1-benzimidazoles having the formula:

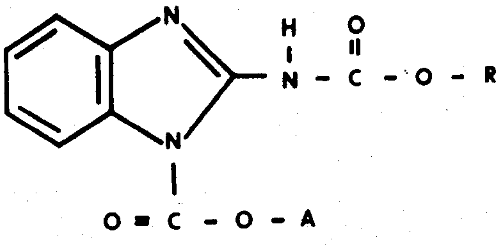

wherein R is a lower alkyl radical, such as $-CH_3$, and A is various organic radicals, hereinafter defined, such as:

$$-CH_2-\overset{O}{\overset{\|}{C}}-O-CH_2CH_3 ,$$

are useful as fungicides and mite ovicides.

An exemplary species of the general class is the compound: 2-(methoxycarbonylamino)-1-benzimidazolecarboxylic acid, ester with ethyl glycolate.

9 Claims, No Drawings

2-(ALKOXYCARBONYLAMINO)-1-BENZIMIDAZOLECARBOXYLIC ACID ESTERS WITH HYDROXYALIPHATIC ACIDS AND DERIVATIVES THEREOF

CROSS REFERENCE TO RELATED APPLICATIONS

This application is a continuation-in-part of my copending application Ser. No. 116,247, filed Feb. 17, 1971, now abandoned, which is a continuation-in-part of my application Serial No. 776,273, filed Nov. 15, 1968, now abandoned.

BACKGROUND OF THE INVENTION

This invention relates to a group of substituted 2-alkoxycarbonylamino-1-benzimidazoles and to methods of using these compounds as fungicides and mite ovicides.

The survival of man is dependent in a large measure upon his ability to protect from the various agents of destruction, plants and their products which satisfy his basic needs. With the rapidly increasing population of the world, it becomes imperative that there be continuing improvements in the efficiency of the materials and the methods employed to provide this protection. These improvements can be in the form of effective control of more kinds of pests or in the form of requiring less material or application effort. The materials and methods of this invention represent marked advances in all of these possible areas of improvement, as will be explained more fully.

It has been discovered that application of the compounds of this invention by the methods of this invention entirely precludes or reduces damage to plants and inanimate organic materials due to fungi and mites. Fungus mycelia are killed or prevented from developing further by the presence of one or more of the compounds, i.e., the compounds are fungicidal or fungistatic. Adult mites that have been contacted with a compound of this invention lay eggs which fail to produce young mites. Also, eggs that have been treated fail to hatch normally.

SUMMARY OF THE INVENTION

It has been found that the above outstanding fungicidal and mite ovicidal activity can be obtained by applying to the locus of fungus and/or mite infestation, an effective amount of a compound represented by the following formula:

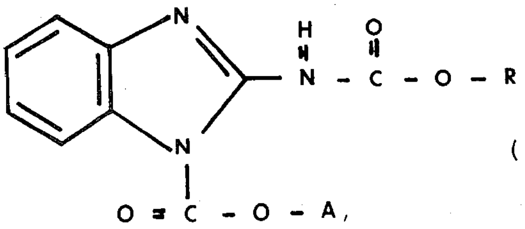

(I)

wherein:

1. R is methyl, ethyl, isopropyl or secondary butyl;
2. A is selected from the group consisting of (a) 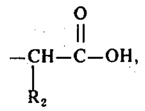

(b) 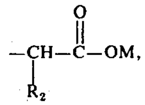

(c) 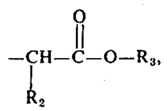 and (d) 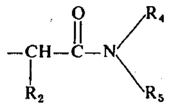

3. $R_2$ is hydrogen, or alkyl of 1 though 14 carbon atoms;
4. $R_3$ is alkyl of 1 through 4 carbon atoms, alkenyl of 3 or 4 carbon atoms, or alkynyl of 3 or 4 carbon atoms;
5. $R_4$ and $R_5$ are hydrogen, alkyl of 1 through 4 carbon atoms, alkenyl of 3 or 4 carbon atoms, alkynyl of 3 or 4 carbon atoms, or taken together can form a 3 through 7-membered ring;
6. M is (i) an alkali metal cation, (ii) an ion selected from ammonium ion, methylammonium ion, dimethylammonium ion, trimethylammonium ion and tetramethylammonium ion;

with the proviso that A contains from 2 through 17 carbon atoms.

The preferred compounds are those in which R is methyl and A has 2 through 10 carbon atoms. The most preferred compounds are:

2-(Methoxycarbonylamino)-1-benzimidazolecarboxylic acid, ester with ethyl glycolate;
2-(Isopropoxycarbonylamino)-1-benzimidazolecarboxylic acid, ester with ethyl glycolate;
2(Methoxycarbonylamino)-1-benzimidazolecarboxylic acid, ester with methyl glycolate;
2-(Isopropoxycarbonylamino)-1-benzimidazolecarboxylic acid, ester with methyl glycolate;
2-(Methoxycarbonylamino)-1-benzimidazolecarboxylic acid, ester with ethyl lactate;
2-(Ethoxycarbonylamino)-1-benzimidazolecarboxylic acid, ester with ethyl lactate;
2-(Methoxycarbonylamino)-1-benzimidazolecarboxylic acid, ester with N,N-dimethylglycolamide; and
2-(Isopropoxycarbonylamino)-1-benzimidazolecarboxylic acid, ester with N,N-dimethylglycolamide.

It should be understood that the compounds of this invention exist in two tautomeric forms, i.e.,

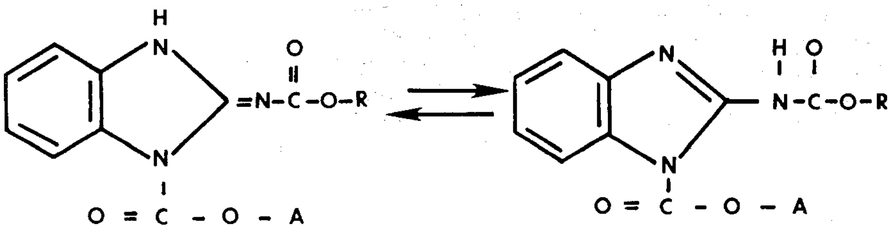

The compounds of the invention are applied in sufficient amounts to control fungi and mites. The amount of compound necessary to control both fungi and mites is referred to herein as an "effective amount." The amount of compound necessary to control fungi or mites is referred to herein as a "fungicidal amount" or a "mite ovicidal amount," respectively.

DETAILED DESCRIPTION OF THE INVENTION

Preparation of the Compounds

The compounds of this invention can be prepared by reacting 2-benzimidazolecarbamates with a chloroformate derived from a hydroxyaliphatic acid ester in the presence of an acid acceptor, such as sodium bicarbonate, according to the equation:

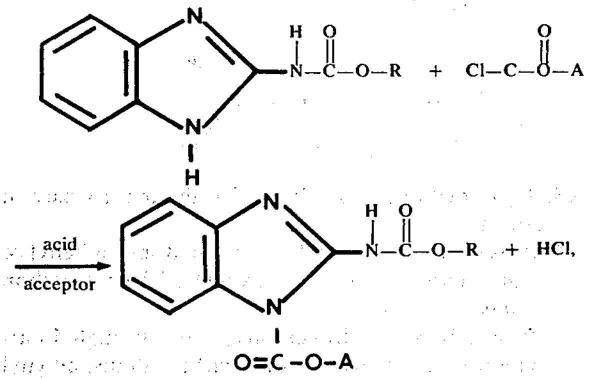

wherein R and A are as previously defined. Methods for preparing the starting 2-benzimidazolecarbamates are disclosed in U.S. Pat. No. 3,010,968, issued Nov. 28, 1961 to Loux.

In general, a mixture of (1) one mole equivalent of a suitable chloroformate derived from a hydroxyaliphatic acid ester, such as an alkyl or alkenyl glycolate or lactate chloroformate, (2) about 1.1 mole equivalent of a 2-benzimidazolecarbamate, and (3) about one mole equivalent of an acid acceptor, such as sodium bicarbonate or sodium carbonate, is stirred in a non-reactive solvent, such as acetone or chloroform, at a temperature between 25°C. to 100°C. for 0.25 minutes to 24 hours. The resulting mixtures is then filtered. If the product is insoluble in the particular reaction solvent used, the filter cake is dried, slurried in water, filtered, and dried, yielding the pure product. On the other hand, if the product is soluble in the reaction solvent, the filtrate is evaporated, thereby yielding a crude product. This is then recrystallized from a suitable solvent, such as methylene chloride, or a suitable combination of solvents, such as a mixture of chloroform and hexane, to yield the pure product.

The preparation of the compounds of this invention is illustrated by the following examples, the amounts being given in terms of parts by weight unless otherwise specified.

EXAMPLE 1

A mixture of 4 parts of ethyl glycolate chloroformate, 4.5 parts of 2-(methoxycarbonylamino)benzimidazole, 4 parts of sodium bicarbonate and 50 parts of acetone is heated at gentle reflux with stirring for 3 hours. The hot mixture is filtered and sufficient water is added to the cooled filtrate to effect precipitation. On filtration, there is obtained 3.9 parts of 2-(methoxycarbonylamino)-1-benzimidazolecarboxylic acid, ester with ethyl glycolate, m.p.: 144°–145°C.

The compounds of Examples 2-12 can be synthesized by the method of Example 1, substituting the appropriate 2(alkoxycarbonylamino)benzimidazole (A) for 2-(methoxycarbonylamino)benzimidazole and the appropriate chloroformate (B) for ethyl glycolate chloroformate:

EXAMPLE 2

(A) 2-(Ethoxycarbonylamino)benzimidazole
(B) Ethyl glycolate chloroformate
(C) 2-(Ethoxycarbonylamino)-1-benzimidazole-carboxylic acid, ester with ethyl glycolate.

EXAMPLE 3

(A) 2-(Methoxycarbonylamino)benzimidazole
(B) Ethyl lactate chloroformate
(C) 2-(Methoxycarbonylamino)-1-benzimidazole-carboxylic acid, ester with ethyl lactate.

EXAMPLE 4

(A) 2-(Methoxycarbonylamino)benzimidazole
(B) Allyl glycolate chloroformate
(C) 2-(Methoxycarbonylamino)-1-benzimidazole-carboxylic acid, ester with allyl glycolate.

EXAMPLE 5

(A) 2-(Isopropoxycarbonylamino)benzimidazole
(B) Hydroxymethyl morpholino ketone chloroformate
(C) 2-(Isopropoxycarbonylamino)-1-benzimidazole-carboxylic acid, ester with hydroxymethyl morpholino ketone.

EXAMPLE 6

(A) 2-(Ethoxycarbonylamino)benzimidazole
(B) Glycolamide chloroformate
(C) 2-(Ethoxycarbonylamino)-1-benzimidazole-carboxylic acid, ester with glycolamide.

EXAMPLE 7

(A) 2-(Ethoxycarbonylamino)benzimidazole
(B) Propargyl glycolate chloroformate
(C) 2-(Ethoxycarbonylamino)-1-benzimidazole-carboxylic acid, ester with propargyl glycolate.

EXAMPLE 8

(A) 2-(Methoxycarbonylamino)benzimidazole
(B) Ethyl 2-hydroxybutyrate chloroformate
(C) 2-(Methoxycarbonylamino)-1-benzidazole-carboxylic acid, ester with ethyl 2-hydroxybutyrate.

EXAMPLE 9

(A) 2-(Methoxycarbonylamino)benzimidazole
(B) Methyl 2-hydroxypalmitate chloroformate
(C) 2-(Methoxycarbonylamino)-1-benzimidazole-carboxylic acid, ester with methyl 2-hydroxypalmitate.

EXAMPLE 10

(A) 2-(Isopropoxycarbonylamino)benzimidazole
(B) Aziridino hydroxymethyl ketone chloroformate
(C) 2-(Isopropoxycarbonylamino)-1-benzimidazole carboxylic acid, ester with aziridino hydroxymethyl ketone.

EXAMPLE 11

(A) 2-(Methoxycarbonylamino)benzimidazole (B) Hexahydroazepino hydroxymethyl ketone chloroformate
(C) 2-(Methoxycarbonylamino)-1-benzimidazole carboxylic acid, ester with hexahydroazepino hydroxymethyl ketone chloroformate.

EXAMPLE 12

(A) 2-(sec-Butoxycarbonylamino)benzimidazole
(B) Ethyl glycolate chloroformate
(C) 2-(sec-Butoxycarbonylamino)-1-benzimidazolecarboxylic acid, ester with ethyl glycolate.

EXAMPLE 13

(A) 2-(sec-Butoxycarbonylamino)benzimidazole
(B) 3-Butenyl glycolate chloroformate
2-(sec-Butoxycarbonylamino)-1-benzimidazolecarboxylic acid, ester with 3-butenyl glycolate

EXAMPLE 14

(A) 2-(Ethoxycarbonylamino)benzimidazole
(B) 2-Butynyl glycolate chloroformate
(C) 2-(Ethoxycarbonylamino)-1-benzimidazolecarboxylic acid, ester with 2-butynyl glycolate

EXAMPLE 15

(A) 2-(Methoxycarbonylamino)benzimidazole
(B) 1-Propynyl glycolate chloroformate
(C) 2-(Methoxycarbonylamino)-1-benzimidazolecarboxylic acid, ester with 1-propynyl glycolate

EXAMPLE 16

(A) 2-(Methoxycarbonylamino)benzimidazole
(B) N,N-Diallylglycolamide chloroformate
(C) 2-(Methoxycarbonylamino)-1-benzimidazolecarboxylic acid, ester with N,N-diallylglycolamide

EXAMPLE 17

(A) 2-(Ethoxycarbonylamino)benzimidazole
(B) N,N-Di(3-butynyl)glycolamide chloroformate
(C) 2-(Ethoxycarbonylamino)-1-benzimidazolecarboxylic acid, ester with N,N-di(3-butynyl)-glycolamide

EXAMPLE 18

(A) 2-(sec-Butoxycarbonylamino)benzimidazole
(B) N-(2-butenyl)glycolamide chloroformate
(C) 2-(sec-Butoxycarbonylamino)-1-benzimidazolecarboxylic acid, ester with N-(2-butenyl)-glycolamide

EXAMPLE 19

(A) 2-(Isopropoxycarbonylamino)benzimidazole
(B) N-(1-Propynyl)glycolamide chloroformate
(C) 2-(Isopropoxycarbonylamino)-1-benzimidazolecarboxylic acid, ester with N-(1-propynyl)-glycolamide

EXAMPLE 20

(A) 2-(Methoxycarbonylamino)benzimidazole
(B) Butyl glycolate chloroformate
(C) 2-(Methoxycarbonylamino)-1-benzimidazolecarboxylic acid, ester with butyl glycolate

EXAMPLE 21

A solution of 10 parts of 2-(methoxycarbonylamino)-1-benzimidazolecarboxylic acid, ester with tert-butyl glycolate and 1 part of anhydrous p-toluenesulfonic acid in 500 parts of benzene is boiled under reflux for 1 hr. The solution is washed with 100 parts of water and the benzene solution is dried over 25 parts of anhydrous magnesium sulfate. The mixture is filtered and the filtrate is evaporated, yielding 2-(methoxycarbonylamino)-1-benzimidazolecarboxylic acid, ester with glycolic acid as a solid.

EXAMPLE 22

The filtered solution from Example 21 is treated with 1.3 parts of N,N-dimethylamine. The solution is then evaporated yielding the dimethylamine salt of 2-(methoxycarbonylamino)-1-benzimidazolecarboxylic acid, ester with glycolic acid as a white solid.

The following compounds (F) of Examples 23–26 can by synthesized by the methods of Examples 21 and 22 from the appropriate 2-(alkoxycarbonylamino)-1-benzimidazolecarboxylic acid, ester with hydroxyaliphatic acid (D) and the appropriate amine or ammonia (E).

EXAMPLE 23

(D) 2-(Isopropoxycarbonylamino)-1-benzimidazolecarboxylic acid, ester with glycolic acid
(E) Ammonia
(F) The ammonium salt of 2-(Isopropoxycarbonylamino)-1-benzimidazolecarboxylic acid, ester with glycolic acid.

EXAMPLE 24

(D) 2-(Methoxycarbonylamino)-1-benzimidazolecarboxylic acid, ester with glycolic acid
(E) Dimethylamine
(F) The dimethylamine salt of 2-(methoxycarbonylamino)-1-benzimidazolecarboxylic acid, ester with glycolic acid.

EXAMPLE 25

(D) 2-(Ethoxycarbonylamino)-1-benzimidazolecarboxylic acid, ester with glycolic acid
(E) Trimethylamine
(F) The trimethylamine salt of 2-(ethoxycarbonylamino)-1-benzimidazolecarboxylic acid, ester with glycolic acid.

EXAMPLE 26

(D) 2-(Isopropoxycarbonylamino)-1-benzimidazolecarboxylic acid, ester with glycolic acid
(E) Tetramethylammonium hydroxide pentahydrate
(F) The tetramethylammonium salt of 2-(isopropoxycarbonylamino)-1-benzimidazolecarboxylic acid, ester with glycolic acid.

EXAMPLE 27

The filtered solution from Example 21 is treated with 0.69 parts of sodium hydride. After stirring for 4 hrs. the solution is evaporated, yielding the sodium salt of 2-(methoxycarbonylamino)-1-benzimidazolecarboxylic acid, ester with glycolic acid, as a white solid.

The following compounds (L) of Examples 28 and 29 can be prepared by the method of 27 from the appropriate 2-(alkoxycarbonylamino)-1-benzimidazolecarboxylic acid, ester with hydroxyalkanoic acid (J) and alkali metal hydroxide (K).

EXAMPLE 28

(J) 2-(Methoxycarbonylamino)-1-benzimidazolecarboxylic acid, ester with 2-hydroxylbutyric acid
(K) Potassium hydroxide
(L) 2-(Methoxycarbonylamino)-1-benzimidazolecarboxylic acid, ester with 2-hydroxybutyric acid, potassium salt

EXAMPLE 29

(J) 2-(Ethoxycarbonylamino)-1-benzimidazolecarboxylic acid, ester with glycolic acid
(K) Lithium hydroxide
(L) 2-(Ethoxycarbonylamino)-1-benzimidazolecarboxylic acid, ester with glycolic acid, lithium salt Utility of the Compounds It has been found that the compounds of this invention possess outstanding fungicidal and mite ovicidal activity when employed to prevent or mitigate damage to plants and inanimate organic materials. A further aspect of this invention involves methods which when used in conjunction with the compounds of this invention, result in advances in mite and fungus control of great practical importance. A further advantage of the compounds of the invention is that they have a low order of mammalian toxicity. The paragraphs which follow describe in more detail the utility of this invention.

The compounds of the invention control a wide variety of fungus diseases of foliage, fruit, stems and roots of growing plants without damage to the host. Fruits, tubers, bulbs, roots, seeds and other plant parts harvested for food, animal feed or for other purposes are protected from fungus deterioration during processing, distribution and storage. Seeds, tubers, cuttings and other plant propagation materials are protected from fungus attack during handling and storage, as well as in the soil after planting. Wood, fabric, fiber board, paper and other industrial materials are protected from unsightly stain and destructive decay caused by fungi. Luggage, shoes, shower curtains, carpets, mats, clothing and other useful household, public or industrial items are protected from rot, fungus stains and mold growth. Painted surfaces are protected from stain and discoloration by incorporation of a compound of this invention in the paint formulation.

The many fungi against which the compounds of this invention are active may be represented by, but are not intended to be limited to, the following: *Venturia inaequalis*, which causes apple scab; *Podosphaera leucotricha*, which causes powdery mildew on apple; *Uromyces phaseoli*, which causes bean rust; *Cercospora apii*, which causes early blight of celery; *Cercospora beticola*, which causes leaf spot of sugar beets; *Sclerotinia sclerotiorum*, which causes rot of vegetable crops, such mildew lettuce, beans, carrots, and celery; *Colletotrichum* spp., which cause anthracnose of fruits and vegetables, such as beans, tomatoes and coffee; *Septoria apii*, which causes late blight of celery; *Cerospora musae*, which causes Sigotoka disease of banana; *Piricularia sp.*, which causes Johnson spot on banana; *Erysiphe cichoracearum*, which causes powdery mildew on cantaloupe and other cucurbit crops; *Penicillium digitatum*, *Phomopsis spp.*, and *Diplodia natalensis*, which cause fruit rots on citrus; *Ceratostomella ulmi*, which causes Dutch elm disease; *Sphaerotheca humuli*, which causes powdery mildrw on roses; *Diplocarpon rosae*, which causes black spot on roses; *Ramularia sp.*, which causes leaf spots on ornamental plants; *Botrytis cinerea*, which causes blossom and fruit rots of ornamentals, fruits and vegetables; *Uncinula necator*, which causes powdery mildew on grapes; *Guignardia bidwellii* which causes grape black rot; *Melonconium fuligineum, which causes white rot of grapes; Coccomyces hiemalis*, which causes cherry leaf spot; *Cytospora sp.*, which cause cankers of trees; *Cladosporium carpophilum*, which causes peach scab; *Fusicladium effusum*, which causes pecan scab; *Erysiphe graminis*, which causes powdery mildew on cereals; *Monolinia* (*Sclerotinia*) *laxa* and *M. fructicola*, which cause brown rot of stone fruits, such as peaches, cherries and apricots; *Pseudopeziza ribes*, which causes leaf spot on gooseberry; *Piricularia oryzae*, which causes rice blast; *Puccinia rubigovera P. coronata* and *P. glumarum*, which cause leaf rusts of wheat, oats and grasses, respectively; *Puccinia graminis tritici*, which causes stem rust of wheat; *Claviceps purpurea*, which causes ergot of rye and grasses; *Aspergillus niger*, which causes cotton boll rot as well as decay following wounding in many plant tissues; *Aspergillus flavus*, which causes mold growth on peanuts, as well as on other food and feed materials; *Aspergillus terreus*, which is common in soil and attacks vegetable matter; *Tilletia caries* and other *Tilletia* species, which cause common bunt of wheat; *Ustilago tritici*, *Ustilago nigra*, *Ustilago avena* (and other *Ustilago* species), which cause loose smut of wheat, barley, and oats, respectively; *Urocystis tritici* and other *Urocystis* species, which cause smuts on grain crops; *Sphacelotheca sorghi*, which causes covered smut of sorghum; *Ustilago hordei* and *Ustilago kolleri*, which cause covered smut of barley and oats, respectively; *Pithomyces chartorum*, which is present in turf, pastures, and other grassy areas and is known to have several secondary effects; *Gloeodes pomigena*, which causes sooty blotch on apples; *Physalospora obtusa*, which causes black rot on apples; *Microthyriella rubi*, which causes flyspeck on apples; various species of *Rhizoctonia*, *Fusarium* and *Verticillum* present in soil and attacking the roots or other underground parts and the vascular system of a variety of plants; various species of *Penicillium* growing on such things as fabric, fiber board, leather goods and paint; species of *Myrothecium* attacking such items as shower curtains, carpets, mats and clothing.

The mite ovicidal action of the compounds of this invention is useful in preventing the development of damaging populations of mites or in causing the gradual reduction of existing populations. The movement of mites is limited. Thus, an increase in population or the continuation of a high population in a particular locus depends largely upon the hatching of eggs laid in that locus.

Mite eggs do not hatch to produce living young if these eggs are treated with one of these compounds, or if they are laid on a surface containing one of these compounds. Further, the eggs will not hatch if they are laid by a female mite that has been in contact with one of these compounds, or are laid by a female mite that is ingesting or has recently ingested food such as plant juices containing one of these compounds. This interference with the hatching of eggs prevents the population from increasing significantly beyond that present at the time of treatment. Also, this ovidical action, along with the high natural mortality of adults, can largely eliminate mites from an already infested area over a relatively short period of time. Further as long as the compounds are present on the surface the mites occupy or remain in their food supply, new populations cannot develop.

Many species of mites which cause damage to fruits, field crops, vegetabels, and ornamentals under a wide variety of circumstances, are controlled by the compounds and methods of this invention. The extent of the practical utility of the mites control obtained is represented by, but is not intended to be limited to, the following listing of specific susceptible mites along with the types of damage that they can cause: *Panonychus ulmi* (European red mite) and *Tetranychus urticae* (two-spotted mite) which are commonly called "orchard mites"; these mites attack a great many deciduous tree fruits including apples, pears, cherries, plums and peaches; *Tetranychus atlanticus* (Atlantic or strawberry mite), *T. cinnabarinus* (carmine spider mite) and *T. pacificus* (Pacific mite); these mites attack cotton and numerous other crop plants; *Paratetranychus citri* (citrus red mite) and others which attack citrus; *Phyllocuptruta sleivora* which causes citrus russet; *Bryobia praetiosa (clover mite) which attacks clover, alfalfa and other crops; Phyllosoptruta oleivora*, the citrus rust mite; *Aceria neocynodomis* which attacks grasses and other plants; *Tyrophagus lintneri* which is a serious pest in stored foods and on cultivated mushrooms and *Lepidoglyphus destructor* which injures Kentucky bluegrass in storage.

The compounds of this invention when applied by certain of the methods of this invention enter and move freely within plants, i.e., they are systemic. Thus both fungi and mites can be controlled on plant parts well removed from the point of application. In view of this activity, the compounds can be applied to seeds; thus, the treatment of cucumber seeds with a few grams per 50 kilograms of seed of a compound of this invention provides control of powdery mildew (*Erysiphe cichoracearum*) and spider mites such as *Tetranychus urticae* on the resulting plants for periods in excess of 40 days. Applications to soil also provide control of certain foliage diseases and mites on plants growing in the treated soil. Spray or dust treatments of plant foliage and stems impart protection against both fungi and mites to other parts of the plant not actually sprayed and to new foliage developing later.

There are important practical advantages associated with the use of an effective systemic pesticide. Thus, successful application to seed as described above results in great savings in chemical and application costs. Soil applications which effectively protect entire plants for an extended period also represent similar savings. Distribution within the plant following foliage treatment eliminates the need for frequent retreatment to protect rapidly growing tissue. Also, materials within the plant are not subject to removal by rainfall. Similarly, movement or translocation of the chemical within the plant can provide protection to those parts of the plant that may not have been covered by the original spray application. This is of particular importance with plants of dense growth character resisting the intrusion of the spray and also to tall plants, such as trees, where the spray will not reach to the top.

An additional valuable characteristic of the compounds of this invention is their ability to prevent the spread of or to kill fungus infection already established within a plant, i.e. they are curative. Thus, the compounds need not be applied until after conditions develop which permit the actual initiation of fungus attack. This means that, under some circumstances, it is possible to avoid applying any chemical during the entire life of the crop. In other cases, only a part of the normal full schedule of pesticide application is required.

Therefore great savings both in chemical cost and application labor are possible with compounds capable of systemic and curative performance. Another saving is afforded by the compounds of this invention through the fact that both fungi and mites are controlled by applications of a single chemical.

The compounds of this invention provide protection from damage caused by fungi, mites or both when applied to the proper locus by the methods described hereinafter and at a sufficient rate to exert the desired fungicidal and mite ovicidal effect. They are especially suited for the protection of living plants such as fruit-bearing trees, nut-bearing trees, ornamental trees, forest trees, vegetable crops, horticultural crops (including ornamentals, small fruits and berries), fiber crops, grain and seed crops, sugarcane, sugar beets, pineapple, forage and hay crops, beans, peas, soybeans, peanuts, potatoes, sweetpotatoes, tobacco, hops, turf and pasture.

Living plants may be protected from fungi and mites by applying one or more of the compounds of this invention to the soil in which they are growing or in which they may subsequently be seeded or planted; or to seeds, tubers, bulbs or other plant reproductive parts prior to planting; as well as to foliage, stems and fruit of the living plant. Living plants can also be protected by dipping the root system or physically injecting the chemical or chemicals into roots or stems.

Soil applications are made from dusts, granules, pellets, slurries or solutions. Preferred rates for application of the compounds of this invenetion to soil in which plants are or will be growing range from 1.0 to 500 parts per million by weight of the soil in which the roots are or will be growing. More preferred use rates are in the range of 2.0 to 50 parts per million, and the most preferred rates are in the range of 4.0 to 25 parts per million.

Preferred rates for application to seeds, tubers, bulbs or other plant reproductive parts, range from 1 to 6000 grams of active compound of this invention per 50 kilograms of planting material treated. More preferred rates are in the range of 3 to 3000 grams of active compound per 50 kilograms. The most preferred rates are in the range of 20 to 1500 grams per 50 kilograms. Applications are made from dusts, slurries or solutions. Such treatments protect the treated parts themselves from damage due to fungi, mites, or both, and in addition, impart extended protection against both types of pests to the resulting new plants.

Preferred rates for application of the compounds of this invention to foliage, stems and fruit of living plants range from0.012 to 20 kilograms of active ingredient per hectare. More preferred rates are in the range of 0.025 to 10 kilograms per hectare and the most preferred rates are in the range of 0.05 to 5 kilograms per hectare. The optimum amount within this range depends upon a number of variables which are well known to those skilled in the art of plant protection. These variables include, but are not limited to, the disease to be controlled, weather conditions expected, the type of crop, stage of development of the crop, and the interval between applications. Applications within the range given may need to be repeated one or many more times at intervals of 1 to 60 days. Applications are made from dusts, slurries or solutions.

Preferred rates for dip applications to roots of living plants are in the range of 100 to 18,000 grams of active ingredient per 400 liters of water or other liquid carrier. More preferred rates are in the range of 200 to 9,000 grams per 400 liters and the most preferred rates are in the range of 400 to 4500 grams per 400 liters.

Preferred rates for injection into the roots or stems of living plants are in the range of 1.0 to 10,000 parts per million of water or other liquid carrier. More preferred rates are in the range of 2.0 to 5,000 parts per million. The most preferred rates are in the range of 4.0 to 1,000 parts per million.

Plant parts such as fruits, tubers, bulbs, foliage roots and the like, harvested for food or feed, are protected from decay and other deterioration caused by fungi or mites during processing, distribution and storage by treatment with an active compound of this invention. The plant parts to be so protected can be dipped in a liquid bath containing the active ingredient, dusted with a finely divided preparation of the active ingredient, sprayed, misted with an aerosol containing the compound, or enclosed in wrapping or packing materials impregnated with the active compound.

If a liquid bath is used, it can contain an amount of the active ingredient in the range of 1 to 5,000 parts per million of the weight of the fluid. A more preferred range for the bath is 5 to 2,500 parts per million, and the most preferred range is 10 to 1,000 parts per million.

Dusts as well as wrapping or packing materials used for this type of application can contain 0.1 to 10 percent of the active ingredient. The most preferred rates are in the range of 1 to 5 percent.

Wood, leather, fabric, fiber board, paper and other industrial materials of an organic nature can be protected from decomposition or discoloration by fungi and infestation by mites by coating, incorporating or impregnating with an effective amount of one or more of the compounds of this invention. The coating can be accomplished by dipping, spraying, flooding, misting (as with an aerosol) or dusting the material to be protected with a suitable composition containing the active ingredient. The preferred use rates for the active ingredient in the treating preparation actually applied to the material to be protected are in the range of 0.5 to 95 percent by weight. More preferred rates are in the range of 1 to 50 percent, with the most preferred rates being in the range of 2 to 25 percent.

Where incorporation or impregnation procedures are to be employed, use rates may be expressed in terms of the amount of active ingredient introduced into the material to be protected. The use rates for these types of applications are in the range of 1 to 10,000 parts per million.

Luggage, shoes, shower curtains, carpets, mats, clothing and other useful household, public or industrial items are protected from rot, fungus stains and unsightly mold growth as well as infestation by mites by the active compounds of this invention. Again, either surface or deep protection can be obtained. Surface treatment is by dips, washes, sprays, aerosols or dust applications. Deep treatment is accomplished by penetrating solutions. Sprays, dips and washes contain the active compound of the invention at rates of 10 to 5000 parts per million. Fluids for aerosol application and dusts contain 2.0 to 25 percent by weight. Penetrating solvent solutions contain an amount of the active ingredient that results in a deposit of 1 to 10,000 parts per million in the material to be protected.

Painted surfaces can be protected from unsightly stain and mold growth by incorporating in the pain formulation, prior to application, 1 to 10,000 parts per million of an active compound of this invention. More preferred rates are in the range of 10 to 1,000 parts per million and the most preferred rates are in the range of 20 to 500 parts per million. Such treatments with the compounds of this invention also protect the paint while still in the can from deterioration by fungi.

Damage by mites to stored organic products such as grain, seed, bulbs, tubers, meat or animal hides is kept to a minimum by treating the floors, walls, partitions, and other parts of warehouses or other structures with one or more of the active compounds. Applications are made by the use of dusts, sprays, or aerosols with preferred use rates in the range of 1.0 to 1000 grams of the active compound of this invention per 100 square meters of surface to be kept free of excessive mite populations.

As was previously set forth, the compounds of this invention are especially suited for use on living plants. Application to the foliage, stems and fruit of plant at the rate indicated above is generally accomplished by employing sprays, dusts or aerosols containing the proper amount of active ingredient. For the control of mites and fungi which are regularly present, applications often start prior to the time that the problem actually appears and continue on a pre-determined schedule. Such a procedure is termed "preventive" or "protective."

With the compounds of this invention, successful control of plant diseases can also be accomplished by applications made after symptoms have appeared. Fungus mycelia within the plant tissue are actually killed. This approach or effect is termed "curative" or "eradicant" and permits the user to realize considerable savings.

Curative control of plant diseases with the compounds of this invention is enhanced if the treated plant parts are moist for one or more periods of 2 to 12 hours each soon after the active compound is applied. Often the slow drying of an original spray treatment or naturally occurring rains, mists, fogs or dews will accomplish this. Under other circumstances, such as during dry periods or in shelters such as greenhouses, it is necessary to keep the plants moist by some special effort for best results.

The compounds of this invention can be used to prevent the spoilage of animal feeds. In particular, when mixed with the feed, they provide more efficient and longer lasting protection without harm or injury to livestock that consume it. The compounds of this invention may be conveniently formulated for this use in a number of the ways previously disclosed and these formulations may be mixed directly with mixed feed, newly harvested hay and newly harvested grain. These compounds effectively prevent the spoilage of corn, sorghum, wheat, barley, oats, rye and other grains that may be used as livestock feed.

Under normal conditions, these compounds may be incorporated into feeds at rates of from 0.01% to 0.25% with excellent results. Higher rates may be required under very damp conditions.

These compounds can also be used to improve the performance of other feed additives, such as sodium propionate, by mixing the two additives directly, or by adding them separately to the feed to be protected.

The compounds of this invention have an activity which relates to the treatment of sewage, soil or other substances in which natural oxidation processes occur. More specifically, the addition of these benzimidazole compounds to such substrates increases the rate and magnitude of oxidation processes.

Sewage is a dilute aqueous solution of organic wastes which must be treated to prevent pollution of natural water sources. During sewage treatment, complex organic and inorganic molecules are oxidized to simpler molecules, such as carbon dioxide, water and nitrates. Two common techniques for increasing the oxidation, or decomposition, rate of sewage in modern sewage treatment plants are the use of a trickling filter and the use of aeration tanks. The addition of benzimidazole compounds to sewage adds a new technique for increasing the decomposition rate of sewage, and can be used to increase the effects achieved in trickling filters and aeration tanks. When benzimidazole compounds are added to sewage, the result is an increase in the rate of oxygen utilization in the sewage which signifies an increase in the decomposition rate of the sewage.

The addition of benzimidazole compounds to soil results in a more rapid and complete oxidation of fertilizer nitrogen into nitrates. The formation of nitrates in the soil is related to soil temperature and decreases with decreasing temperature. Below 45°C. very little nitrate forms. Consequently, in cold climates where the growing season is short, the addition of benzimidazole compounds to nitrogenous fertilizers will result in a more rapid and complete conversion into nitrates and thereby stimulate plants to mature faster.

When the compounds of this invention are applied, their activity can be enhanced by mixing same with pest control adjuvants or modifiers to provide compositions in the form of dusts, granules, pellets, water dispersible powders, high strength concentrates, aqueous dispersions or emulsions, and solutions or dispersions in organic liquids.

Thus, the compounds of formula (I) can be used with a carrier or diluent agent such as a finely divided solid, an organic liquid, water, a wetting agent, a dispersing agent, an emulsifying agent, or any suitable combination of these.

Compositions of the invention, especially liquids and wettable powders, contain as a conditioning agent one or more surface-active agents, sometimes called surfactants, in amounts sufficient to render a given composition containing the compounds of formula (I) readily dispersible in water or in oil.

The surface-active agent used in this invention can be a wetting, dispersing or an emulsifying agent which will assist dispersion of the compound. The surface-active agent or surfactant can include such anionic, cationic and non-ionic agents as have heretofore been generally employed in plant control compositions of similar type. Suitable surface-active agents are set forth, for example, in "Detergents and Emulsifiers" 1967 Annual by John W. McCutcheon, Inc.

In general, less than 10 percent by weight of the surface-active agent will be used in compositions of this invention and ordinarily the amount of surface-active agents will range from 1–5 percent but may even be less than 1 percent by weight.

Additional surface-active agents can be added to the formulations or to the final sprays to increase the ratio of surfactant: active ingredient up to as high as 5:1 by weight. Such compositions have a greater fungicidal effectiveness than can be expected from a consideration of the activity of the components used separately. When used at higher rates it is preferred that the surfactant be present in the range of one-fifth to five parts surfactant for each one part of active agent.

A. WETTABLE POWDERS

Wettable powders are water-dispersible compositions containing the active material, an inert solid extender, and one or more surfactants to provide rapid wetting and prevent heavy flocculation when suspended in water.

The inert extenders which are preferred for use in the wettable powders of this invention containing the compounds of formula (I) are of mineral or vegetable origin.

The classes of extenders suitable for the wettable powder formulations of this invention are the natural clays, diatomaceous earth, synthetic mineral fillers derived from silica and silicate, cellusosic or starch flours, and solid sugars. Most preferred fillers for this invention are kaolinites, attapulgite clay, montmorillonite clays, synthetic silicas, synthetic magnesium silicate, calcium sulfate dihydrate, coated calcium carbonate, corn cob flour, walnut shell flour, tobacco stem dust, and cane sugar.

Suitable surfactants for use in such compositions are those listed by J. W. McCutcheon in "Detergents and Emulsifiers" 1967 Annual. Among the more preferred surfactants are the non-ionic and anionic type, and those most suitable for the preparation of the dry, wettable products of this invention are solid forms of compounds known to the art as wetters and dispersants. Occasionally a liquid, non-ionic compound classified primarily as an emulsifier may serve as both wetter and dispersant.

Most preferred wetting agents are alkylbenzene- and alkylnaphthalene sulfonates, sulfated fatty alcohols, long-chain acid esters of sodium isethionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalenesulfonates, sodium naphthalenesulfonate, polymethylene bisnaphthalenesulfonate, and sodium N-methyl-N-(long-chain acid)-taurates.

Wetting and dispersing agents in these preferred wettable powder compositions of this invention are usually present at concentrations of from about 0.5 weight percent to 5 weight percent. The inert extender then completes the formulation. Where needed, 0.1 weight percent to 1.0 weight percent of the extender may be replaced by a corrosion inhibitor or an anti-foaming agent or both.

Thus, wettable powder formulations of the invention will contain from about 25 to 90 weight percent active material, from 0.5 to 2.0 weight percent wetting agent, from 0.25 to 5.0 weight percent dispersant, and from 9.25 to 74.25 weight percent inert extender, as these terms are described above.

When the wettable powder contains a corrosion inhibitor or an anti-foaming agent or both, the corrosion inhibitor will not exceed about 1 percent of the composition, and the anti-foaming agent will not exceed about 0.5 percent by weight of the composition, both replacing equivalent amounts of the inert extender.

The following examples illustrate the use of the compounds. All percentages are on a weight basis unless otherwise indicated.

Example 30

| | Percent |
|---|---|
| 2-(Methoxycarbonylamino)-1-benzimidazole-carboxylic acid, ester with ethyl glycolate | 50 |
| Sodium dioctyl sulfosuccinate | 3 |
| Methyl cellulose | 1 |
| Cane Sugar | 46 |

The above ingredients are blended and ground in a hammer mill. This material is further ground in a fluid energy mill such as a micronizer until substantially all particles of active ingredients are 10 microns or less.

The above 50 percent wettable powder formulation is dispersed in water to give an active ingredient concentration of 30 grams per 100 liters of water. Eight uniform apple trees of the same variety are selected for testing. Four of these are sprayed to run-off, which is approximately 2500 liters per hectare, at weekly intervals during the growing season with the above formulation, and the other four trees are left unsprayed.

By the end of the season the unsprayed trees have developed very high populations of orchard mites and are highly infected with apple scab, caused by *Venturia inaequalis*, and apple powdery mildew caused by *Podosphaera leucotricha*. Due to the feeding of the mites, the foliage is russeted and drops prematurely. Also, the untreated trees have poor twig growth and small, spotted fruit because of the fungus diseases.

The trees sprayed with the formulation described above are essentially free of mites, their eggs, powdery mildew, and apple scab. As a result of the excellent mite and disease control, the sprayed trees have foliage of a thrifty, dark green color, and they exhibit good twig growth and fruit size.

EXAMPLE 31

The following compounds may be substituted one at a time for 2-(Methoxycarbonylamino)-1-benzimidazolecarboxylic acid, ester with ethyl glycolate of Example 30 in like amount by weight, and when used as as above give similar results:

| | Compound |
|---|---|
| 1 | 2-(Isopropoxycarbonylamino)-1-benzimidazolecarboxylic acid, ester with ethyl glycolate |
| 2 | 2-(Methoxycarbonylamino)-1-benzimidazolecarboxylic acid, ester with methyl glycolate |
| 3 | 2-(Isopropoxycarbonylamino)-1-benzimidazolecarboxylic acid, ester with methyl glycolate |
| 4 | 2-(Methoxycarbonylamino)-1-benzimidazolecarboxylic acid, ester with ethyl lactate |
| 5 | 2-(Ethoxycarbonylamino)-1-benzimidazolecarboxylic acid, ester with ethyl lactate |
| 6 | 2-(Methoxycarbonylamino)-1-benzimidazolecarboxylic acid, ester with N,N-dimethylglycolamide |
| 7 | 2-(Isopropoxycarbonylamino)-1-benzimidazolecarboxylic acid, ester with N,N-dimethylglycolamide. |

Example 32

| | Percent |
|---|---|
| 2-(Ethoxycarbonylamino)-1-benzimidazole-carboxylic acid, ester with ethyl lactate | 75 |
| Oleic acid ester of sodium isethionate | 3 |
| Methyl cellulose | 1 |
| Corn cob flour | 21 |

After blending, the above ingredients are ground as in Example 30 until essentially all particles of active ingredient are 10 microns or less.

A vineyard of grapes in California is selected as a test site. Alternate rows are sprayed to run off with water containing a suspension of the wettable powder described above along with a polyhydric alcohol ester surface-active agent ("Trem" 014). The amount of formulation used is such as to provide 300 ppm of the active compound. The amount of Trem 014 is 400 ppm in the final spray. The spray is applied at weekly intervals at a rate of 900 liters per hectare from early spring until harvest. At harvest the berries from the treated rows are large and firm and the clusters are well filled out. On the other hand, the berries from the untreated rows are small, cracked, and rotting because of infections by the fungus *Uncinula necator* which causes powdery mildew and the fungus *Botrytis cinerea* which rots the fruit.

Example 33

| | Percent |
|---|---|
| 2-(Isopropoxycarbonylamino)-1-benzimidazole-carboxylic acid, ester with ethyl glycolate | 70 |
| Sodium lauryl sulfate | 1 |
| Methyl cellulose | 0.3 |
| Kaolinite clay | 28.7 |

The above ingredients are ground as in Example 30 until substantially all particles of active ingredient are 10 microns or less.

Test plots are established in a rice field. The plots are sprayed with water containing a suspension of the wettable powder described above along with a modified phthalic glycerol alkyd resin surface-active agent ("Triton" B1956). The amount of the wettable powder used in such as to provide 1.5 grams of the active compound of this invention per liter of water. The amount of Triton B1956 is 400 ppm in the final spray. The spray is applied weekly intervals at the rate of 900 liters per hectare. The remainder of the field is left unsprayed. Three months after the start of the test, the sprayed plots are healthy and growing well. The untreated areas, on the other hand, are seriously damaged by the rice blast fungus, (*Piricularia oryzae*) which greatly reduces yeild.

Example 34

| | Percent |
|---|---|
| 2-(Methoxycarbonylamino)-1-benzimidazole-carboxylic acid, ester with ethyl glycolate | 25 |
| Sodium dioctyl sulfosuccinate | 3 |
| Methyl cellulose | 1 |
| Walnut shell flour | 71 |

The above ingredients are blended and are ground in a hammermill to produce a finely divided wettable powder.

A uniform field planting of cantaloupe in North Carolina is inoculated with the powdery mildew fungus (*Erysiphe cichoracearum*). After 10 days this organism has become well established in the plants.

As this time alternate rows are sprayed with water containing a suspension of the wettable powder prepared as described above and an added amount of a polyhydric alcohol ester surface-active agent (Trem 014). The concentration of this chemical suspension is such as to give 600 ppm of the active compound of this formulation and 400 ppm of the surfactant. The spray is applied at a volume of 1410 liters per hectare. The remaining rows are left unsprayed.

After another 15 days the unsprayed rows are heavily damaged by powdery mildew and some of the plants are dying. The sprayed rows, however, are healthy and growing rapidly. The results indicate that the active compound of the suspension acts as a curative fungicide.

EXAMPLE 35

The following compounds may be substituted one at a time for 2-methoxycarbonylamino-1-benzimidazolecarboxylic acid, ester with ethyl glycolate, of Example 30 in like amount by weight, and when used as above in Example 34 give similar results:

| Compound | |
|---|---|
| 1 | 2-(Isopropoxycarbonylamino)-1-benzimidazolecarboxylic acid, ester with ethyl glycolate |
| 2 | 2-(Methoxycarbonylamino)-1-benzimidazolecarboxylic acid, ester with methyl glycolate |
| 3 | 2-(Isopropoxycarbonylamino)-1-benzimidazolecarboxylic acid, ester with methyl glycolate |
| 4 | 2-(Methoxycarbonylamino)-1-benzimidazolecarboxylic acid, ester with ethyl lactate |
| 5 | 2-(Ethoxycarbonylamino)-1-benzimidazolecarboxylic acid, ester with ethyl lactate |
| 6 | 2-(Methoxycarbonylamino)-1-benzimidazolecarboxylic acid, ester with N,N-dimethylglycolamide |
| 7 | 2-(Isopropoxycarbonylamino)-1-benzimidazolecarboxylic acid, ester with N,N-dimethylglycolamide. |

Example 36

| | Percent |
|---|---|
| 2-(Ethoxycarbonylamino)-1-benzimidazolecarboxylic acid, ester with ethyl lactate | 85 |
| Purified, partially desulfonated, sodium ligninsulfonate | 3 |
| Sodium dioctyl sulfosuccinate | 3 |
| Diatomaceous silica | 9 |

After blending, the above ingredients are ground until substantially all particles of active ingredient are 5 microns or less.

A test is established in a field planting of celery in Florida. Random plots are established and sprayed with water containing a suspension of the wettable powder described above along with a blend of aromatic sulfonate and ethylene oxide derivatives ("Agrimul" GM). The amount of wettable powder used is such as to provide 300 ppm of active compound, and the amount of Agrimul GM used is such as to provide 300 ppm in the final spray. The spray is applied weekly at the rate of 1000 liters per hectare. The remainder of the field is left unsprayed.

Three months after the first spray application, the sprayed celery plots are in a healthy condition and obviously growing well. The untreated portions of the field, on the other hand, are seriously infested with the early blight fungus (*Cercospora apii*) and the late blight fungus (*Septoria apii*). These diseases cause the death of much of the foliage and reduce the growth and marketable volume of the crop.

Example 37

| | Percent |
|---|---|
| 2-(Isopropoxycarbonylamino)-1-benzimidazolecarboxylic acid, ester with N,N-dimethylglycolamide | 70 |
| Citric acid | 5 |
| Sodium alkylnaphthalenesulfonate | 0.5 |
| Diatomaceous silica | 22.5 |

The above ingredients are blended and ground as in Example 30 until substantially all particles of active ingredient are 10 microns or less.

The formulation of this example is useful in controlling peach scab caused by the fungus *Cladosporium carpophilum*. This is demonstrated by a field study in which random trees in a peach planting are sprayed, starting in the spring, with water containing a suspension of the wettable powder described in the example along with an acid complex organic phosphate ester surface-active agent ("Gafac" RE-610).

The amount of the wettable powder used is such as to provide 30 grams of the active compound of this invention per 100 liters of water. The amount of Gafac RE-610 employed is 400 ppm in the final spray.

The spray is applied on a normal peach fungicide schedule at the rate of 2000 liters per hectare of peach trees. The remaining trees in the planting are left unsprayed.

At the time of harvest fruit on the treated trees is healthy and attractive to consumers. Conversely, fruit from the euntreated trees is spotted with scab and of reduced market value.

B. HIGH-STRENGTH COMPOSITION AND AQUEOUS SUSPENSION CONCENTRATES

High-strength compositions generally consist of 90 to 99.5 percent active ingredient and 0.5 to 10 percent of a liquid or solid surfactant such as those described by McCutcheon in "Detergents and Emulsifiers" 1967 Annual. Such high-strength compositions can often be used in a manner similar to the wettable powders but they are also suitable for further formulation.

The aqueous suspension concentrates are prepared by mixing together and sandgrinding an aqueous slurry of water-insoluble active ingredient in the presence of dispersing agents. Thus there is obtained a concentrated slurry of very finely divided particles in which the active ingredient is substantially all below 5 microns in size. This concentrated aqueous suspension is characterized by its extremely small particle size so that upon diluting and spraying, a very uniform coverage is obtained.

These aqueous suspension concentrates will contain from 15 to 40 percent of active ingredient, from 45 to 70 percent water with the remainder made up of surfactants, corrosion inhibitors, and suspending agents.

Suspensions in organic liquids can be prepared in a similar manner such as by replacing the water with mineral oil.

Example 38

| | Percent |
|---|---|
| 2-(Isopropoxycarbonylamino)-1-benzimidazolecarboxylic acid, ester with N,N-dimethylglycolamide | 90 |
| Oleic acid ester of sodium isethionate | 2 |
| Purified sodium ligninsulfonate | 8 |

These ingredients are blended and ground in a hammer mill and then in a fluid energy mill such as a micronizer until substantially all particles of active ingredient are 10 microns or less. The fluid energy grinding may be omitted if the high strength composition is to be used for further formulation.

The formulation of this example is useful in controlling Sigatoka disease of banana caused by the fungus *Cercospora musae*. This is demonstrated by a field test in which designated areas in a banana plantation are treated with 800 grams of the active ingredient of this invention per hetare and an equal amount of a polyhydric alcohol ester surface active agent (Trem 014) applied to the foliage in an amount of water sufficient to assure good distribution. The treatment is applied at intervals of 14 days.

Four months after the start of the test the banana plants in the treated plots are free from disease, whereas, the untreated plants are heavily damaged by Sigatoka disease.

EXAMPLE 39

The following compounds may be substituted one at a time for 2-(isopropoxycarbonylamino)-1-benzimidazolecarboxylic acid, ester with N,N-dimethylglycolamide, of Example 38 in like amount by weight, and when used as above give similar results:

| Compound | |
|---|---|
| 1 | 2-(Methoxycarbonylamino)-1-benzimidazolecarboxylic acid, ester with ethyl glycolate |
| 2 | 2-(Isopropoxycarbonylamino)-1-benzimidazolecarboxylic acid, ester with ethyl glyclolate |
| 3 | 2-(Methoxycarbonylamino)-1-benzimidazolecarboxylic acid, ester with methyl glycolate |
| 4 | 2-(Isopropoxycarbonylamino)-1-benzimidazolecarboxylic acid, ester with methyl glycolate |
| 5 | 2-(Methoxycarbonylamino)-1-benzimidazolecarboxylic acid, ester with ethyl lactate |
| 6 | 2-(Ethoxycarbonylamino)-1-benzimidazolecarboxylic acid, ester with ethyl lactate |
| 7 | 2-(Methoxycarbonylamino)-1-benzimidazolecarboxylic acid, ester with N,N-dimethylglycolamide |

Example 40

| | Percent |
|---|---|
| 2-(Methoxycarbonylamino)-1-benzimidazolecarboxylic acid, ester with methyl glycolate | 25 |
| Polyoxyethylene (4) lauryl ether | 8 |
| Paraffinic oil | 67 |

The above ingredients are sand ground until substantially all particles of active ingredient are 5 microns or less.

The suspension is added to water at a rate of 300 ppm of active ingredient in the final spray. A modified phthalic glycerol alkyd resin surface-active agent ("Triton" B 1956) is added in an amount to give 400 ppm in the final spray. This suspension is used to spray (to the point of run-off) alternate trees in a field planting of apples. Sprays are applied at weekly intervals from April 25 until June 6. From June 6 until the end of the season, the sprays are applied at intervals of two weeks. The remaining trees in the planting are left unsprayed.

In early September all trees are carefully examined. Trees that were sprayed with the compound of this invention are healthy and free of mite infestation and fungus damage. The fruit on the sprayed trees is unblemished and of good size. The foliage of the unsprayed trees, on the other hand, is heavily infested with the apple scab fungus (*Venturia inaequalis*) and the powdery mildew fungus (*Podosphaera leucotricha*). Also, the leaves of the unsprayed trees are badly infested with European red mites (*Panonychus ulmi*). The fruit on the unsprayed trees is spotted with scab and of small size.

EXAMPLE 41

The following compounds may be substituted one at a time for 2-(methoxycarbonylamino)-1-benzimidazolecarboxylic acid, ester with methyl glycolate, of Example 40 in like amount by weight, and when used as above give similar results:

| Compound | |
|---|---|
| 1 | 2-(Methoxycarbonylamino)-1-benzimidazolecarboxylic acid, ester with ethyl glycolate |
| 2 | 2-(Isopropoxycarbonylamino)-1-benzimidazolecarboxylic acid, ester with ethyl glycolate |
| 3 | 2-(Isopropoxycarbonylamino)-1-benzimidazolecarboxylic acid, ester with methyl glycolate |
| 4 | 2-(Methoxycarbonylamino)-1-benzimidazolecarboxylic acid, ester with ethyl lactate |
| 5 | 2-(Ethoxycarbonylamino)-1-benzimidazolecarboxylic acid, ester with ethyl lactate |
| 6 | 2-(Methoxycarbonylamino)-1-benzimidazolecarboxylic acid, ester with N,N-dimethylglycolamide |
| 7 | 2-(Isopropoxycarbonylamino)-1-benzimidazolecarboxyliic acid, ester with N,N-dimethylglycolamide |

Example 42

| | Percent |
|---|---|
| 2-(Methoxycarbonylamino)-1-benzimidazolecarboxylic acid, ester with N,N-dimethylglycolamide | 30 |
| Calcium magnesium ligninsulfonate | 15 |
| Hydrated attapulgite | 1.5 |
| Water | 53.5 |

The above ingredients are sand ground until substantially all particles of active material are 5 microns or less.

Alternate rose bushes growing in a greenhouse are sprayed at weekly intervals with the formulation described above. The rate of 300 ppm of active ingredient is mixed with 600 ppm of "Triton B1956" in the final water spray. After two months of this program the treated plants are healthy, with dark green attractive foliage and are growing well. The untreated plants, on the other hand, have much foliage discolored and curled due to infection by the rose powdery mildew organism, *Sphaerotheca humuli*. Other foliage on the untreated plants is yellowed due to attack by the Atlantic mite (*Tetranychus atlanticus*). Due to the extensive foliage damage, the plants not treated with the compound of this invention grow more slowly than the protected plants.

C. DUSTS

Dusts are dense powder compositions which are intended for application in dry form, in accordance with the preferred compositions and methods of the invention. Dusts are characterized by their free-flowing and rapid settling properties so that they are not readily windborne to areas where their presence is not desired. They contain primarily an active material and a dense, free-flowing, solid extender.

Their performance is sometimes aided by the inclusion of a wetting agent, and convenience in manufacture frequently demands the inclusion of an inert, absorptive grinding aid. For the dust compositions of this invention, the inert extender may be either of vegetable or mineral origin, the wetting agent is preferably anionic or non-ionic, and suitable absorptive grinding aids are of mineral origin.

Suitable classes of inert solid extenders for use in the dust compositions are those organic or inorganic powders which possess high bulk density and are very free-flowing. They are also characterized by possessing relatively low surface areas and are poor in liquid absorption. Suitable classes of grinding aids are natural clays, diatomaceous earths, and synthetic mineral fillers derived from silica or silicate. Among ionic and non-ionic wetting agents, the most suitable are the members of the group known to the art as wetting agents and emulsifiers. Although solid agents are preferred because of ease in incorporation, some liquid non-ionic agents are also suitable in the dust formulations.

Preferred inert solid extenders for the dusts of this invention are micaceous talcs, pyrophyllite, dense kaolin clays, tobacco dust, corn cob flour, and cane sugar.

Preferred grinding aids are attapulgite clay, diatomaceous silica, synthetic fine silica and synthetic calcium and magnesium silicates. Preferred wetting agents are those previously described under wettable powder formulations.

The inert solid extenders in the dusts of this invention are usually present in concentrations of from about 30 to 95 weight percent of the total composition. The grinding aid will usually constitute 0 to 50 weight percent of the composition, and the wetting agent will constitute from about 0 to 1.0 weight percent of the composition. Dust compositions can also contain other surfactants such as dispersing agents in concentrations of up to about 0.5 weight percent.

The wettable powders described above can also be used in the preparation of dusts. While such wettable powders could be used directly in dust form, it is more advantageous to dilute them by blending with the dense dust diluent. In this manner, dispersing agents, corrosion inhibitors, and anti-foam agents may also be found as components of a dust.

Thus, the dust compositions of this invention will comprise about 5 to 20 weight percent active material, 0 to 50 weight percent absorptive filler, 0 to 1.0 weight percent wetting agent, and about 30 to 95 weight percent dense, free-flowing dust diluent, as these terms are used herein. Such dust formulations can contain, in addition, minor amounts of dispersants, corrosion inhibitors, and anti-foam agents, derived from the wettable powders used to make the dusts.

Example 43

| | Percent |
|---|---|
| 2-(Methoxycarbonylamino)-1-benzimidazole-carboxylic acid, ester with ethyl lactate | 10 |
| Calcium stearate coated calcium carbonate | 45 |
| Micaceous talc | 45 |

The above ingredients are blended and ground in a hammer mill until a uniform dust is obtained.

A uniform cherry orchard in Michigan is selected for the test. Alternate trees are dusted every 14 days at the rate of 1 kilogram per tree with the above dust formulation. The remaining trees are left unprotected.

On September 1 the trees are examined. The trees that had been dusted with the compound of this invention are green and healthy, with all leaves remaining on the trees. At this time the foliage of the unprotected trees is largely discolored due to attack by the leaf spot fungus (*Coccomyces hiemalis*) and the two spotted mite (*Tetranychus telarius*). Further, much of the foliage of the unprotected trees has fallen due to the effect of the two pests.

EXAMPLE 44

The following compounds are substituted one at a time for 2-(methoxycarbonylamino)-1-benzimidazolecarboxylic acid, ester with ethyl lactate, of Example 43 in like amount by weight, and when used as above give similar results:

| Compound | |
|---|---|
| 1 | 2-(Methoxycarbonylamino)-1-benzimidazolecarboxylic acid, ester with ethyl glycolate |
| 2 | 2-(Isopropoxycarbonylamino)-1-benzimidazolecarboxyl acid, ester with ethyl glycolate |
| 3 | 2-(Methoxycarbonylamino)-1-benzimidazolecarboxylic acid, ester with methyl glycolate |
| 4 | 2-(Isopropoxycarbonylamino)-1-benzimidazolecarboxy acid, ester with methyl glycolate |
| 5 | 2-(Ethoxycarbonylamino)-1-benzimidazolecarboxylic acid, ester with ethyl lactate |
| 6 | 2-(Methoxycarbonylamino)-1-benzimidazolecarboxylic acid, ester with N,N-dimethylglycolamide |
| 7 | 2-(Isopropoxycarbonylamino)-1-benzimidazolecarboxylic acid, ester with N,N-dimethylglycolamide. |

Example 45

| | Percent |
|---|---|
| Wettable powder of Example 33 | 7.2 |
| Micaceous talc | 92.8 |

A finely divided dust is obtained by blending the above ingredients and then passing the mixture thru a deagglomerator such as an Entoleter mill.

A single row is selected in a sugar beet field for treatment with the dust of this formulation. After the sugar beets are one month old and a few lesions of *Cercospora beticola* have become evident as spots on the leaves, weekly dust treatments are applied to the selected row. The 7.2 percent dust of this formulation is applied by a tractor mounted single row dusting device which delivers approximately 20 kilograms per hectare. There is some drift to adjacent rows but the remainder of the field is left untreated. At harvest the foliage is examined and the beets are dug and weighed. The treated row is a vigorous healthy row with lush green foliage, and the beets are large and normal. The adjacent rows are spotted with numerous leaf spot leasions and the remainder of the field is almost entirely defoliated. A few yound leaves on the untreated beets are still green but all of the older leaves are dried up. Beets from the untreated rows are less than half normal size.

Example 46

| | Percent |
|---|---|
| Wettable powder of Example 30 | 20 |
| Cane sugar | 80 |

A blend of the above ingredients is ground in a hammer mill to obtain a uniform dust.

Alternate rose bushes growing in a greenhouse are dusted lightly at weekly intervals with the formulation described above. After two months of this program the treated plants are healthy, with dark green attractive foliage and are growing well. The untreated plants, on the other hand, have much foliage discolored and curled due to infection by the rose powdery mildew organism, *Sphaerotheca humuli*. Other foliage on the untreated plants is yellowed due to attack by the Atlantic mite (*Tetranychus atlanticus*). Due to the extensive foliage damage, the plants not treated with the compound of this invention grow more slowly than the protected plants.

D. GRANULES AND PELLETS

Granules and pellets are physically stable, particulate compositions containing a compound of formula (I) which adheres to or is distributed through a basic matrix of a coherent, inert carrier with macroscopic dimensions. In order to aid leaching of the active ingredient from the granule or pellet, a surfactant can be present.

For the compounds of this invention, the inert carrier may be of mineral or vegetable origin, and the surfactant is a compound known in the art as a wetting agent. Such compounds are listed by J. W. McCutcheon in "Detergents and Emulsifiers" 1967 Annual.

Suitable carriers are natural clays, cellulosic materials some pyrophyllites and vermiculite. Suitable wetting agents are anionic or non-ionic.

For the granule compositions of this invention, most suitable carriers are of two types. The first may be porous, absorptive, preformed granules, such as preformed and screened granular attapulgite heat expanded, granular, screened vermiculite, granular cellulosic materials, or dense, non-porous solids to which a coating of active ingredient will adhere. On the absorptive carriers, a solution of the active agent can be sprayed and will be absorbed up to 25 weight percent active ingredient, relative to the total weight of granules. Alternatively, a non-porous carrier may be mixed with active ingredient and surfactant and while so mixing, be sprayed with a small amount or organic liquid which is a solvent for the active ingredient. The second types of carrier, which are also suitable for pellets, are initially powdered kaolin clays, cellulose, hydrated attapulgite, or bentonite clays in the form of sodium, calcium or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 30–60 mesh.

The most suitable wetting agents for the granular compsoitions of this invention depend upon the type of granule used. When preformed granules are sprayed with active material in liquid form the most suitable wetting agents are non-ionic, liquid wetters miscible with the solvent. These are compounds more generally known to the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil-soluble petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid non-ionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 weight percent active material, about 0 to 5 weight percent wetting agent, and about 65 to 95 weight percent inert mineral or vegetable carrier, as these terms are used herein.

Example 47

| | Percent |
|---|---|
| 2-(Methoxycarbonylamino)-1-benzimidazole-carboxylic acid, ester with ethyl glycolate | 10 |
| Calcium ligninsulfonate | 5 |
| Corn cob granules | 85 |

The active ingredient is dissolved in a suitable organic solvent and this solution is sprayed onto the dry ingredients as they are tumbled in a rotary mixer.

Four similar potted bean plants (one plant per pot) are selected. The soil in two of these pots had been mixed with granules of the formulation described above at a rate to provide 30 parts per million of active ingredient by weight in the total amount of soil in the pot. The remaining two pots are left untreated.

Five days after treatment 50 adult mites (*Tetranychus telarius*) are placed on a terminal leaf on each of the test plants. Twenty-four hours later these adult mites, all still alive, are removed in a way which causes no damage to the eggs that have been laid during the twenty-four hour period. The number of eggs laid by each batch of 50 mites is essentially the same. A sufficient time is allowed for all viable eggs to hatch. Counts demonstrate that none of the eggs hatch from among those laid by mites that had fed on foliage from pots with soil containing the compound of this formulation. Hatch to provide living young was complete, on the other hand, among eggs laid by mites similarly handled except that the plants providing sustenance were not in contact with the compound of this formulation. This experiment demonstrates systemic movement in plants and mite ovicide effect.

EXAMPLE 48

The following compounds may be substituted one at a time for 2-(methoxycarbonylamino)-1-benzimidazolecarboxylic acid, ester with ethyl glycolate, of Example 47 in like amount by weight, and when used as above give similar results:

| Compound | |
|---|---|
| 1 | 2-(Isopropoxycarbonylamino)-1-benzimidazolecarboxylic acid, ester with ethyl glycolate |
| 2 | 2-(Methoxycarbonylamino)-1-benzimidazolecarboxylic acid, ester with methyl glycolate |
| 3 | 2-(Isopropoxycarbonylamino)-1-benzimidazolecarboxylic acid, ester with methyl glycolate |
| 4 | 2-(Methoxycarbonylamino)-1-benzimidazolecarboxylic acid, ester with ethyl lactate |
| 5 | 2-(Ethoxycarbonylamino)-1-benzimidazolecarboxylic acid, ester with ethyl lactate |
| 6 | 2-(Methoxycarbonylamino)-1-benzimidazolecarboxylic acid, ester with N,N-dimethylglycolamide |
| 7 | 2-(Isopropoxycarbonylamino)-1-benzimidazolecarboxylic acid, ester with N,N-dimethylglycolamide. |

Example 49

| | Percent |
|---|---|
| Wettable powder of Example 30 | 20 |
| Cane sugar, 30-60 mesh | 80 |

The above dry ingredients are tumbled in a rotary mixer while being sprayed with an organic liquid such as methylene chloride which is a solvent for the active ingredient. A minimum of solvent is used to avoid aggregating coated particles of the carrier and to insure as hard a coating as possible.

The granules of this formulation are mixed with potting soil in such a quantity to provide 100 parts per million of active ingredient by weight in the total amount of soil in five pots. An additional 5 pots are made up of untreated soil. Cotton is planted and allowed to grow one month in the 10 pots. At the end of one month a spore suspension of *Verticillium alboatrum* is injected with a hypodermic needle into the node at the cotyledonary leaf of each plant. This inoculation method forces the fungus into the vascular system of the plant and assures the production of severe disease symptoms. One month after this inoculation all five cotton plants growing in the treated soil are vigorous and are in all ways normal and healthy. On the other hand, all five plants growing in untreated soil are severely defoliated and dying due to typical Verticillium wilt symptoms.

Example 50

| | Percent |
|---|---|
| 2-(Isopropoxycarbonylamino)-1-benzimidazolecarboxylic acid, ester with N,N-dimethylglycolamide | 25 |
| Hydrated attapulgite | 58 |
| Sodium lauryl sulfate | 2 |
| Powdered kaolinite | 15 |

The above ingredients are blended and ground in a hammer mill. This mixture is moistened with water and granulated in a rotary mixture then dried and screened to give granules which are between 30 and 60 mesh.

A field is selected in Florida that is being prepared for planting cucumbers. One row is treated with this formulation by sprinkling the granules the full length of the field in a band 1 meter wide over the bed at a rate equal to 10 kilograms per 4,000 meters of row. The granules are then mixed to a depth of 5 centimeters. Cucumbers are planted in the entire field and allowed to grow under normal cultivation. By mid-season the cucumbers are severely infected with powdery mildew caused by *Erysiphe cichoracearum*. At harvest time the vines are severely defoliated and the exposed fruit is small and sun scalded. On the other hand, the row of cucumbers which received the soil treatment is free of powdery mildew and supports a healthy normal crop.

EXAMPLE 51

The following compounds are substituted one at a time for 2-(isopropoxycarbonylamino)-1-benzimidazolecarboxylic acid, ester with N,N-dimethylglycolamide of Example 50 in like amount by weight, and when used as above give similar results:

| Compound | |
|---|---|
| 1 | 2-(Methoxycarbonylamino)-1-benzimidazolecarboxylic acid, ester with ethyl glycolate |
| 2 | 2-(Isopropoxycarbonylamino)-1-benzimidazolecarboxylic acid, ester with ethyl glycolate |
| 3 | 2-(Methoxycarbonylamino)-1-benzimidazolecarboxylic acid, ester with methyl glycolate |
| 4 | 2-(Isopropoxycarbonylamino)-1-benzimidazolecarboxylic acid, ester with methyl glycolate |
| 5 | 2-(Methoxycarbonylamino)-1-benzimidazolecarboxylic acid, ester with ethyl lactate |
| 6 | 2-(Ethoxycarbonylamino)-1-benzimidazolecarboxylic acid, ester with ethyl lactate |
| 7 | 2-(Methoxycarbonylamino)-1-benzimidazolecarboxylic acid, ester with N,N-dimethylglycolamide |

In addition to the active ingredient of this invention, conventional insecticides, miticides, bactericides, nematocides, fungicides, or other agricultural chemicals such as fruit-set agents, fruit thinning compounds, fertilizer ingredients and the like can be added to the composition of the active ingredient, so that the compositions can serve useful purposes in addition to the control of fungi and mite infestations.

The following are illustrative of the agricultural chemicals that can be included in the compositions or, additionally, that may be added to sprays containing one or more of the active compounds.

1,2,3,4,10,10-hexachloro-1,4,4a,5,8,8a-hexahydro-1,4-endoexo-5,8-dimethanonaphthalene (aldrin);
1,2,3,4,5,6-hexachlorocyclohexane (lindane);
1-naphthyl methylcarbamate (carbaryl);
0,0-diethyl 0-(2-isopropyl-6-methyl-4-pyrimidinyl) phosphorothioate (diazinon);
diethyl mercaptosuccinate, S-ester with 0,0-dimethyl phosphorodithioate (malathion);
0,0-dimethyl-0-p-nitrophenyl phosphorothioate (methyl parathion);
0,0-diethyl 0-p-nitrophenyl phosphorothioate (parathion);
2,2-dichlorovinyl 0,0-dimethyl phosphate (dichlorvos);
0,0-dimethyl S-(4-oxo-1,2,3-benzotriazin-3(4H)-ylmethyl)-phosphorodithioate (azinphosmethyl);
calcium arsenate;
dibasic lead arsenate;
0,0-diethyl 0(and S)-2-(ethylthio)ethyl phosphorothioates (demeton);

2,4-dinitro-6-sec-butylphenol;
toxaphene;
0-ethyl 0-p-nitrophenylphenylphosphonothioate, or ethyl p-nitrophenyl thionobenzenephosphonate (EPN);
ethyl pyrophosphate; often known as tetraethyl pyrophosphate (TEPP);
4,4′-dichloro-α-(trichloromethyl)benzhydrol (dicofol);
S-methyl-N-[(methylcarbamoyl)oxy]thioacetimidate (methomyl);
S-methyl 1-dimethylcarbamoyl-N-[(methylcarbamoyl-)oxy]thioformimidate (oxamyl);
2-heptadecylimidazoline acetate (glyodin);
bis(dimethylthiocarbamoyl)disulfide; or tetramethylthiuram disulfide (thiram);
metal salts of ethylenebisdithiocarbamic acid or propylenebisdithiocarbamic acids, e.g. manganese, zinc, iron and sodium salts (maneb or zineb);
complex of zineb and polyethylene thiuramdisulfide (metiram); pentachloroitrobenzene;
2-(1-methyl-n-heptyl)-4,6-dinitrophenyl crotonate, with its isomer 4-(1-methyl-n-heptyl)-2,6-dinitrophenyl crotonate (dinocap);
n-dodecylguanidine acetate (dodine);
N-(trichloromethylthio)phthalimide (folpet);
N-[(trichloromethyl)thio]-4-cyclohexene-1,2-dicarboximide (captan);
cis-N-[(1,1,2,2-tetrachloroethyl)thio]-4-cyclohexene-1,2-dicarboximide (captafol);
2,4-dichloro-6-(o-chloroanilino)-α-triazin ("Dyrene");
3,3′-ethylenebis(tetrahydro-4,6-dimethyl-2H-1,3,5-thiadiazine-2-thione);
triphenyltin hydroxide (fentin hydroxide);
1,4-dichloro-2,5-dimethoxybenzene (chloroneb);
triphenyltin acetate (fentin acetate);
2,6-dichloro-4-nitroaniline (dichloran);
N′-dichlorofluoromethylthio-N,N-dimethyl-N′-phenylsulfamide (dichlorofluanid);
hexachlorobenzene;
hexachlorophene;
tetrachloroisophthalonitrile (chlorothalonil);
0-ethyl-S,S-diphenyl-dithiophosphate ("Hinosan");
0-ethyl-S-benzylphenylphosphonothiolate ("Inezin");
2,3-dichloro-1,4-napthoquinone;
copper hydroxide ("Kocide");
tribasic copper sulfate;
fixed copper;
sulfur;
sodium N-methyldithiocarbamate (SMDC);
tetrachloroisophthalonitrile ("Daconil 2787");
methyl-1-(butylcarbamoyl)-2-benzimidazolecarbamate (benomyl);
methyl-2-benzimidazolecarbamate;
2-(4-thioazolyl)-benzimidazole(thiobendazole);
1,2-bis(3-methoxycarbonyl-2-thioureido)-benzene(-methyl thiophonate);
2,3-dihydro-5-carboxanilide-6-methyl-1,4-oxathiin-4,4-dioxide (carboxin dioxide);
streptomycin;
kasugamycin;
2-(2,4,5-trichlorophenoxy)propionic acid;
p-chlorophenoxyacetic acid;
1-naphthaleneacetamide; and
succinic acid 2,2-dimethyl hydrazide
N-(1-naphthyl)acetamide;

The agricultural chemicals listed above are merely exemplary of the compounds which can be mixed with the active compounds of this invention and are not intended to any way limit the invention.

The use of pesticides such as those listed above in combination with a compound within the scope of this invention sometimes appears to greatly enhance the activity of the active compound of the invention. In other words, an unexpected degree of activity is sometimes seen when another pesticide is used along with the methods of this invention.

I claim:

1. A compound having the formula:

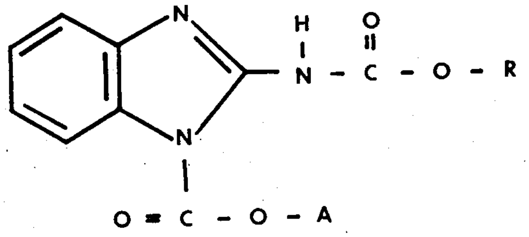

wherein:

1. R is selected from the group consisting of methyl, ethyl, isopropyl, and secondary butyl;
2. A is selected from the group consisting of:

(a) 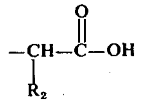

(b) 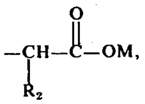, (c) 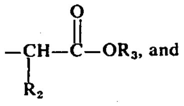, and (d) 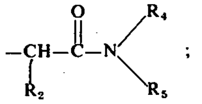;

3. $R_2$ is hydrogen, or alkyl of 1 through 14 carbon atoms;
4. $R_3$ is alkyl of 1 through 4 carbon atoms, alkenyl of 3 or 4 carbon atoms, or alkynyl of 3 or 4 carbon atoms;
5. $R_4$ and $R_5$ are hydrogen, alkyl of 1 through 4 carbon atoms, alkenyl of 3 or 4 carbon atoms or alkynyl or 3 or 4 carbon atoms
6. M is (i) an alkali metal cation, (ii) an ion selected from ammonium ion, methylammonium ion, dimethylammonium ion, trimethylammonium ion and tetramethylammonium ion;

with the proviso that A contains from 2 through 17 carbon atoms.

2. 2-(Methoxycarbonylamino)-1-benzimidazolecarboxylic acid, ester with ethyl glycolate.

3. 2-(Iospropoxycarbonylamino)-1-benzimidazolecarboxylic acid, ester with ethyl glycolate.

4. 2-(Methoxycarbonylamino)-1-benzimidazolecarboxylic acid, ester with methyl glycolate.

5. 2-(Isopropoxycarbonylamino)-1-benzimidazolecarboxylic acid, ester with methyl glycolate.

6. 2-(Methoxycarbonylamino)-1-benzimidazolecarboxylic acid, ester with ethyl lactate.

7. 2-(Ethoxycarbonylamino)-1-benzimidazolecarboxylic acid, ester with ethyl lactate.

8. 2-(Methoxycarbonylamino)-1-benzimidazolecarboxylic acid, ester with N,N-dimethylglycolamide.

9. 2-(Isopropoxycarbonylamino)-1-benzimidazolecarboxylic acid, ester with N,N-dimethylglycolamide.

* * * * *